US010064263B2

(12) United States Patent
Watson et al.

(10) Patent No.: US 10,064,263 B2
(45) Date of Patent: *Aug. 28, 2018

(54) COLD PLASMA TREATMENT DEVICES AND ASSOCIATED METHODS

(71) Applicant: Plasmology4, Inc., Scottsdale, AZ (US)

(72) Inventors: Gregory A. Watson, Lake Mary, FL (US); Robert M. Hummel, Cave Creek, AZ (US); Marc C. Jacofsky, Phoenix, AZ (US); David J. Jacofsky, Peoria, AZ (US)

(73) Assignee: Plasmology4, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/431,208

(22) Filed: Feb. 13, 2017

(65) Prior Publication Data
US 2017/0156200 A1 Jun. 1, 2017

Related U.S. Application Data

(63) Continuation of application No. 14/685,080, filed on Apr. 13, 2015, now Pat. No. 9,570,273, which is a
(Continued)

(51) Int. Cl.
*H01J 37/32* (2006.01)
*H05H 1/46* (2006.01)
(Continued)

(52) U.S. Cl.
CPC ............. *H05H 1/46* (2013.01); *A61L 2/14* (2013.01); *A61N 1/44* (2013.01); *H01J 37/321* (2013.01);
(Continued)

(58) Field of Classification Search
USPC .................................................... 315/111.21
See application file for complete search history.

(56) References Cited

U.S. PATENT DOCUMENTS

| 2,927,322 A | 3/1960 | Simon et al. |
| 3,432,722 A | 3/1969 | Naydan et al. |

(Continued)

FOREIGN PATENT DOCUMENTS

| WO | WO 2005/084569 A1 | 9/2005 |
| WO | WO 2006/116252 | 11/2006 |

(Continued)

OTHER PUBLICATIONS

Dumé, Belle, "Cold Plasmas Destroy Bacteria," article, [online], [retrieved on Jan. 5, 2007], Retrieved from the PhysicsWeb website using Internet <URL:http://physicsweb.org/articles/news7/4/19>.
(Continued)

*Primary Examiner* — Douglas W Owens
*Assistant Examiner* — Srinivas Sathiraju
(74) *Attorney, Agent, or Firm* — Sterne, Kessler, Goldstein & Fox P.L.L.C.

(57) ABSTRACT

A compact cold plasma device for generating cold plasma having temperatures in the range 65 to 120 degrees Fahrenheit. The compact cold plasma device has a magnet-free configuration and an induction-grid-free configuration. An additional configuration uses an induction grid in place of the input electrode to generate the cold plasma. A high voltage power supply is provided that includes a controllable switch to release energy from a capacitor bank to a dual resonance RF transformer. A controller adjusts the energy input to the capacitor bank, as well as the trigger to the controllable switch.

20 Claims, 10 Drawing Sheets

Related U.S. Application Data continuation of application No. 13/620,118, filed on Sep. 14, 2012, now Pat. No. 9,006,976.

(60) Provisional application No. 61/535,250, filed on Sep. 15, 2011.

(51) Int. Cl.
*H05H 1/24* (2006.01)
*A61L 2/14* (2006.01)
*A61N 1/44* (2006.01)

(52) U.S. Cl.
CPC ...... *H01J 37/3244* (2013.01); *H01J 37/3266* (2013.01); *H01J 37/32348* (2013.01); *H05H 1/2406* (2013.01); *H05H 2001/466* (2013.01)

(56) References Cited

U.S. PATENT DOCUMENTS

| | | | |
|---|---|---|---|
| 3,487,414 A | 12/1969 | Booker | |
| 3,735,591 A | 5/1973 | Burkhart | |
| 4,088,926 A | 5/1978 | Fletcher et al. | |
| 4,365,622 A | 12/1982 | Harrison | |
| 4,380,320 A | 4/1983 | Hollstein et al. | |
| 4,422,013 A | 12/1983 | Turchi et al. | |
| 4,473,875 A | 9/1984 | Parsons et al. | |
| 5,079,482 A | 1/1992 | Villecco et al. | |
| 5,216,330 A | 6/1993 | Ahonen | |
| 5,225,740 A | 7/1993 | Ohkawa | |
| 5,304,888 A | 4/1994 | Gesley et al. | |
| 5,698,164 A | 12/1997 | Kishioka et al. | |
| 5,864,267 A | 1/1999 | Hatada et al. | |
| 5,876,663 A | 3/1999 | Laroussi | |
| 5,883,470 A | 3/1999 | Hatakeyama et al. | |
| 5,909,086 A | 6/1999 | Kim et al. | |
| 5,961,772 A * | 10/1999 | Selwyn | H01J 37/32192 |
| | | | 118/723 ER |
| 5,977,715 A | 11/1999 | Li et al. | |
| 6,096,564 A * | 8/2000 | Denes | A61L 2/14 |
| | | | 438/1 |
| 6,099,523 A | 8/2000 | Kim et al. | |
| 6,113,851 A | 9/2000 | Soloshenko et al. | |
| 6,204,605 B1 | 3/2001 | Laroussi et al. | |
| 6,225,593 B1 | 5/2001 | Howieson et al. | |
| 6,228,330 B1 | 5/2001 | Herrmann et al. | |
| 6,262,523 B1 | 7/2001 | Selwyn et al. | |
| 6,441,554 B1 | 8/2002 | Nam et al. | |
| 6,455,014 B1 | 9/2002 | Hammerstrom et al. | |
| 6,611,106 B2 | 8/2003 | Monkhorst et al. | |
| 6,667,007 B1 | 12/2003 | Schmidt | |
| 6,956,329 B2 | 10/2005 | Brooks et al. | |
| 6,958,063 B1 | 10/2005 | Soll et al. | |
| 7,006,874 B2 | 2/2006 | Knowlton et al. | |
| 7,011,790 B2 | 3/2006 | Ruan et al. | |
| 7,037,468 B2 | 5/2006 | Hammerstrom et al. | |
| 7,081,711 B2 | 7/2006 | Glidden et al. | |
| 7,094,314 B2 | 8/2006 | Kurunczi | |
| 7,192,553 B2 | 3/2007 | Crowe et al. | |
| 7,215,697 B2 | 5/2007 | Hill | |
| 7,258,899 B1 | 8/2007 | Sharma et al. | |
| 7,271,363 B2 | 9/2007 | Lee et al. | |
| 7,288,293 B2 | 10/2007 | Koulik et al. | |
| 7,300,436 B2 | 11/2007 | Penny et al. | |
| 7,608,839 B2 | 10/2009 | Coulombe et al. | |
| 7,633,231 B2 * | 12/2009 | Watson | H05H 1/46 |
| | | | 219/121.36 |
| 7,683,342 B2 | 3/2010 | Morfill et al. | |
| 7,691,101 B2 | 4/2010 | Davison et al. | |
| 7,719,200 B2 | 5/2010 | Laroussi | |
| 7,777,151 B2 | 8/2010 | Kuo | |
| 7,785,322 B2 | 8/2010 | Penny et al. | |
| 7,799,290 B2 | 9/2010 | Hammerstrom et al. | |
| 8,005,548 B2 | 8/2011 | Watson | |
| 8,267,884 B1 | 9/2012 | Hicks | |
| 8,294,369 B1 | 10/2012 | Laroussi | |
| 8,359,106 B2 | 1/2013 | Viswanathan et al. | |
| 8,460,283 B1 | 6/2013 | Laroussi et al. | |
| 8,810,134 B2 | 8/2014 | Watson | |
| 9,006,976 B2 * | 4/2015 | Watson | A61M 16/12 |
| | | | 315/111.21 |
| 9,570,273 B2 * | 2/2017 | Watson | A61M 16/12 |
| 2002/0129902 A1 | 9/2002 | Babayan et al. | |
| 2003/0222586 A1 | 12/2003 | Brooks et al. | |
| 2004/0116918 A1 | 6/2004 | Konesky | |
| 2005/0088101 A1 | 4/2005 | Glidden et al. | |
| 2005/0179395 A1 | 8/2005 | Pai | |
| 2006/0189976 A1 | 8/2006 | Karni et al. | |
| 2008/0159925 A1 | 7/2008 | Shimizu et al. | |
| 2009/0012589 A1 | 1/2009 | Watson | |
| 2009/0188626 A1 | 7/2009 | Lu et al. | |
| 2010/0145260 A1 | 1/2010 | Watson | |
| 2010/0133979 A1 | 6/2010 | Lu | |
| 2010/0275950 A1 | 11/2010 | Mack et al. | |
| 2011/0022043 A1 | 1/2011 | Wandke et al. | |
| 2011/0183083 A1 | 7/2011 | Tixhon et al. | |
| 2011/0230819 A1 | 9/2011 | Watson | |
| 2012/0100524 A1 | 4/2012 | Fridman et al. | |
| 2012/0187841 A1 | 7/2012 | Kindel et al. | |
| 2012/0259270 A1 | 10/2012 | Wandke et al. | |
| 2013/0022514 A1 | 1/2013 | Morfill et al. | |
| 2013/0053762 A1 * | 2/2013 | Rontal | A61B 1/0051 |
| | | | 604/24 |
| 2013/0068226 A1 | 3/2013 | Watson et al. | |
| 2013/0068732 A1 | 3/2013 | Watson et al. | |
| 2013/0069530 A1 | 3/2013 | Watson et al. | |
| 2013/0071286 A1 | 3/2013 | Watson et al. | |
| 2013/0072858 A1 | 3/2013 | Watson et al. | |
| 2013/0072859 A1 | 3/2013 | Watson et al. | |
| 2013/0072860 A1 * | 3/2013 | Watson | A61M 16/12 |
| | | | 604/23 |
| 2013/0072861 A1 | 3/2013 | Watson et al. | |
| 2013/0134878 A1 | 5/2013 | Selwyn | |
| 2013/0199540 A1 * | 8/2013 | Buske | A61B 18/042 |
| | | | 128/845 |
| 2014/0000810 A1 | 1/2014 | Franklin et al. | |
| 2014/0354154 A1 | 12/2014 | Watson | |
| 2015/0221476 A1 * | 8/2015 | Watson | A61M 16/12 |
| | | | 315/111.71 |

FOREIGN PATENT DOCUMENTS

| | | |
|---|---|---|
| WO | WO 2007/124910 A2 | 11/2007 |
| WO | WO 2010/107722 A1 | 9/2010 |
| WO | WO 2011/055368 A2 | 5/2011 |
| WO | WO 2011/055369 A2 | 5/2011 |
| WO | WO 2011/076193 A1 | 6/2011 |
| WO | WO 2012/106735 A2 | 8/2012 |
| WO | WO 2012/153132 A2 | 11/2012 |
| WO | WO 2013/101673 A1 | 7/2013 |

OTHER PUBLICATIONS

Gould, Phillip and Eyler, Edward, "Ultracold Plasmas Come of Age," article [online], [retrieved on Jan. 5, 2007], Retrieved from the PhysicsWeb website using Internet <URL:http://physicsweb.org/articles/world/14/3/3>.

Schultz, James, "Cold Plasma Ignites Hot Applications," article, [online], [retrieved on Jan. 5, 2007]Retrieved from the Old Dominion University website using Internet <URL:http://www.odu.edu/ao/instadv/quest/coldplasma.html>.

Lamba, Bikram, "Advent of Cold Plasma," article, [online], [retrieved on Jan. 5, 2007], Retrieved from the PhysOrg.com website using Internet <URL:http//www.physorg.com/printnews.php?newsid=6688>.

Book of Abstracts, 3rd International Conference on Plasma Medicine (ICPM-3), Sep. 19-24, 2010, International Society for Plasma Medicine.

International Search Report dated Aug. 6, 2008 for Appl. No. PCT/US2008/061240, 1 page.

Written Opinion of International Searching Authority dated Aug. 6, 2008 for Appl. No. PCT/US2008/061240, 6 pages.

(56) References Cited

OTHER PUBLICATIONS

Extended European Search Report dated Feb. 8, 2012 for European Patent Appl. No. EP08746627.2, 7 pages.
Pointu et al., "Nitrogen Atmospheric Pressure Post Discharges for Surface Biological Decontamination inside Small Diameter Tubes," *Plasma Process. Polym.* 5:559-568, WILEY-VCH Verlag GmbH, & Co. KGaA, Weinheim (2008).
Chakravarthy et al., "Cold Spark Discharge Plasma Treatment of Inflammatory Bowel Disease in an Animal Model of Ulcerative Colitis," *Plasma Medicine* (1)1:3-19, Begell House, Inc. (2011).
International Search Report dated Jan. 18, 2013 for App. No. PCT/US2012/55569, 5 pages.
Written Opinion of International Searching Authority dated Jan. 18, 2013 for Appl. No. PCT/US2012/55569, 9 pages.
Fridman et al., "Comparison of Direct and Indirect Effects of Non-Thermal Atmospheric-Pressure Plasma on Bacteria," *Plasma Processl Polym.*, 4, 370-375, 6 pages, WILEY-VCH Verlag GmbH & Co. KGaA, Weinheim (2007).
Alexander Fridman, "Plasma Chemistry," pp. 263-271, Cambridge University Press, 2008, 9 pages.
O'Connell et al., "The role of the relative voltage and phase for frequency coupling in a dual-frequency capacitively coupled plasma," *Applied Physics Letters*, 93 081502, 3 pages, American Institute of Physics (Aug. 25, 2008).
Nie et al., "A two-dimensional cold atmospheric plasma jet array for uniform treatment of large-area surfaces for plasma medicine," *New Journal of Physics*, 11 115015, 14 pages, IOP Publishing Ltd and Deutsche Physikalische Gesellschaft (2009).
Pompl et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).
Walsh et al., "Three distinct modes in a cold atmospheric pressure plasma jet." *J. Phys. D.: Appl. Phys.* 43 075201, 14 pages, IOP Publishing Ltd (Feb. 3, 2010).
Ricci el al., "The effect of stochastic electrical noise on hard-to-heal wounds," *Journal of Wound Care*, 8 pages, 19:3 Mark Allen Publishing Ltd ( Mar. 2010).
U.S. Appl. No. 61/485,747, filed May 13, 2011, inventor Thomas J. Sheperak, 14 pages.
Liu et al., "Sub-60° C. atmospheric helium-water plasma jets: modes, electron heating and downstream reaction chemistry," *J. Phys. D: Appl. Phys.* 44 345203, 13 pages, IOP Publishing Ltd. (Aug. 11, 2011).
Pei et al., "Inactivation of a 25.5 µm *Enterococcus faecalis* biofilm by a room-temperature, battery-operated, handheld air plasma jet," *J. Phys. D. Appl. Phys.*, 45 165205, 5 pages, IOP Publishing Ltd (Apr. 4, 2012).
Walsh el al., "Chaos in atmospheric-pressure plasma jets," *Plasma Sources Sci. Technol.*, 21 034008, 8 pages, IOP Publishing Ltd (May 2, 2012).
Banu, et al., "Cold Plasma as a Novel Food Processing Technology," *International Journal of Emerging trends in Engineering and Development*, Issue 2, vol. 4, ISSN 2249-6149, pp. 803-818, 16 pages (May 2012).

Dobrynin, et al., "Live Pig Skin Tissue and Wound Toxicity of Cold Plasma Treatment," *Plasma Medicine*, 1(1):93-108, 16 pages, Begell House, Inc. (2011).
Fernández, et al., "The inactivation of *Salmonella* by cold atmosphere plasma treatment," *Food Research International*, 45:2, 678-684, 7 pages, Elsevier Ltd. (Mar. 2012).
Tien, et al., "The Bilayer Lipid Membrane (BLM) Under Electrical Fields," *IEEE Transactions on Dielectrics and Electrical Institute*, 10:5, 717-727, 11 pages (Oct. 2003).
Jayaram, et al.., "Optimization of Electroporation Waveforms for Cell Sterilization," *IEEE Transactions on Industry Applications*, 40:6, 1489-1497, 9 pages (2004).
Fridman, et al., "Use of Non-Thermal Atmospheric Pressure Plasma Discharge for Coagulation and Sterilization of Surface Wounds," *IEEE International Conference on Plasma Science*, Abstract, p. 257, 1 page (Jun. 2005).
Fridman, et al., "Use of Non-Thermal Atmospheric Pressure Plasma Discharge for Coagulation and Sterilization of Surface Wounds," 6 pages (Jun. 2005).
Fridman, et al., "Blood Coagulation and Living Tissue Sterilization by Floating-Electrode Dielectric Barrier Discharge in Air," *Plasma Chem Plasma Process*, 26: 425-442, 18 pages, Springer Science Business Media, Inc. (2006).
Gurol, et al., "Low Temperature Plasma for decontamination of *E. coli* in milk," *International Journal of Food Microbiology*, 157: 1-5, 5 pages, Elsevier B.V. (Jun. 2012).
Lado, el al., "Alternative food-preservation technologies: efficacy and mechanisms," *Microbes and Infection*, 4: 433-440 8 pages, Elsevier SAS (2002).
Leduc, et al., "Cell permeabilization using a non-thermal plasma," *New Journal of Physics*, 11: 115021, 12 pages, IOP Publishing Ltd and Deutsche Physikalische Gesellschaft (2009).
Machado, et al., "Moderate electric fields can inactivate *Escherichia coli* at room temperature," *Journal of Food Engineering*, 96: 520-527, 8 pages, Elsevier Ltd. (2009).
Li, et al., "Optimizing the distance for bacterial treatment using surface micro-discharge plasma," *New Journal of Physics*, 14: 023058, 11 pages, IOP Publishing Ltd and Deutsche Physikalische Gesellschaft (Feb. 2012).
Morfill, et al., "Nosocomial infections—a new approach towards preventive medicine using plasmas," *New Journal of Physics*, 11: 115019, 10 pages, IOP Publishing Ltd and Deutsche Physikalische Gesellschaft (2009).
Nian, et al., "Decontamination of *Salmonella* on Sliced Fruits and Vegetables Surfaces using a Direct-Current, Atmospheric-Pressure Cold Plasma," *IEEE International Conference on Plasma Science*, p. 1, 1 page (Jun. 2011).
Toepfl, et al., "High intensity pulsed electric fields applied for food preservation," *Chemical Engineering and Processing*, 46: 537-546, 10 pages, Elsevier B.V. (2007).
Extended Search Report dated Dec. 23, 2014 for Appl. No. EP 12 83 2476, 7 pages.
European Search Report dated Feb. 27, 2015 for Appl. No. EP 14 19 5019, 6 pages.

\* cited by examiner

COLD PLASMA TREATMENT DEVICES AND ASSOCIATED METHODS

CROSS REFERENCE TO RELATED APPLICATIONS

The present application is a continuation of U.S. Non-Provisional application Ser. No. 14/685,080, filed Apr. 13, 2015, which is a continuation of U.S. Non-Provisional application Ser. No. 13/620,118, filed Sep. 14, 2012, which claims the benefit under 35 U.S.C. § 119(e) of U.S. Provisional Patent Application No. 61/535,250 entitled "Harmonic Cold Plasma Devices and Associated Methods", filed on Sep. 15, 2011, all of which are hereby expressly incorporated by reference in their entirety.

This application is related to U.S. patent application Ser. No. 13/149,744, filed May 31, 2011, U.S. patent application Ser. No. 12/638,161, filed Dec. 15, 2009, U.S. patent application Ser. No. 12/038,159, filed Feb. 27, 2008, and U.S. Provisional Application No. 60/913,369, filed Apr. 23, 2007, each of which are herein incorporated by reference in their entireties.

BACKGROUND

Field of the Art

The present invention relates to devices and methods for creating cold plasmas, and, more particularly, to such devices that are hand-held and methods for using same.

Background Art

Atmospheric pressure hot plasmas are known to exist in nature. For example, lightning is an example of a DC arc (hot) plasma. Many DC arc plasma applications have been achieved in various manufacturing processes, for example, for use in forming surface coatings. Atmospheric pressure cold plasma processes are also known in the art. Most of the at or near atmospheric pressure cold plasma processes are known to utilize positive to negative electrodes in different configurations, which release free electrons in a noble gas medium.

Devices that use a positive to negative electrode configuration to form a cold plasma from noble gases (helium, argon, etc.) have frequently exhibited electrode degradation and overheating difficulties through continuous device operation. The process conditions for enabling a dense cold plasma electron population without electrode degradation and/or overheating are difficult to achieve.

Different applications and treatment protocols require different cold plasma settings. Therefore, it would be beneficial to provide a device for producing a cold plasma that overcomes the difficulties inherent in prior known devices, as well as provide a straightforward approach to the requirements of different treatment protocols.

BRIEF SUMMARY OF THE INVENTION

An embodiment of a cold plasma device is described that has a housing having a high voltage electrical inlet port and a gas compartment, with the gas compartment being a magnet-free environment and having a gas inlet port and a gas outlet port. The embodiment also has an electrode disposed within the gas compartment, wherein the electrode is coupled to the high voltage electrical inlet port. The electrode is configured to generate cold plasma for release via the gas outlet port, with the cold plasma having a temperature in the range of 65 to 120 degrees Fahrenheit.

An embodiment of a cold plasma device is described that has a housing having a high voltage electrical inlet port and a gas compartment, with the gas compartment being an induction-grid-free environment and having a gas inlet port and a gas outlet port. The embodiment also has an electrode disposed within the gas compartment, wherein the electrode is coupled to the high voltage electrical inlet port. The electrode is configured to generate cold plasma for release via the gas outlet port, with the cold plasma having a temperature in the range of 65 to 120 degrees Fahrenheit.

An embodiment of a cold plasma device is described that has a housing having a high voltage electrical inlet port and a gas compartment having a gas inlet port and a gas outlet port. The embodiment also has a modular electrode disposed within the gas compartment, wherein the modular electrode is coupled to the high voltage electrical inlet port. The modular electrode is configured for easy insertion and removal from the gas compartment. The modular electrode is further configured to generate cold plasma for release via the gas outlet port, with the cold plasma having a temperature in the range of 65 to 120 degrees Fahrenheit.

An embodiment of a cold plasma high voltage power supply is described. The cold plasma high voltage power supply has a capacitor charging power supply with one or more command inputs and an output. The cold plasma high voltage power supply also includes a capacitor bank having one or more capacitors, with the capacitor bank being coupled to the output of the capacitor charging power supply. The cold plasma high voltage power supply also includes a controllable switch having an input port, an output port and a control port, with the controllable switch coupled to the capacitor bank. The cold plasma high voltage power supply also includes a double tuned RF transformer having an input and an output, with the input coupled to the output port of the controllable switch, and the double tuned RF transformer configured to resonate at a first frequency and at a second frequency. The cold plasma high voltage power supply also includes a controller configured to provide commands to the one or more command inputs of the capacitor charging power supply, and to provide a trigger pulse to the control port of the controllable switch.

An embodiment of a cold plasma method is described that includes a step of providing gas to a gas compartment via a gas inlet port, the gas compartment being a magnet-free environment located within a housing having a high voltage electrical inlet port coupled to an electrode disposed within the gas compartment. The embodiment also includes a step of providing a pulsed voltage to the electrode via the high voltage electrical inlet port to thereby generate cold plasma for release via a gas outlet port of the gas compartment, the cold plasma having a temperature in a range of 65 to 120 degrees Fahrenheit.

An embodiment of a cold plasma method is described that includes a step of providing gas to a gas compartment via a gas inlet port, the gas compartment being an induction-grid-free environment located within a housing having a high voltage electrical inlet port coupled to an electrode disposed within the gas compartment. The embodiment also includes a step of providing a pulsed voltage to the electrode via the high voltage electrical inlet port to thereby generate cold plasma for release via a gas outlet port of the gas compartment, the cold plasma having a temperature in a range of 65 to 120 degrees Fahrenheit.

An embodiment of a cold plasma method is described that includes a step of providing energy from a capacitor charging power supply to a capacitor bank having one or more capacitors. The embodiment also includes steps of forwarding, using a controllable switch, the energy from the capacitor bank to a double tuned RF transformer to thereby generate a rich harmonic output voltage, and outputting the rich harmonic output voltage from the double tuned RF transformer to a cold plasma device.

DETAILED DESCRIPTION OF THE INVENTION

Cold temperature atmospheric pressure plasmas have attracted a great deal of enthusiasm and interest by virtue of their provision of plasmas at relatively low gas temperatures. The provision of a plasma at such a temperature is of interest to a variety of applications, including wound healing, anti-bacterial processes, various other medical therapies and sterilization.

Cold Plasma Application Device

Figure 1A:
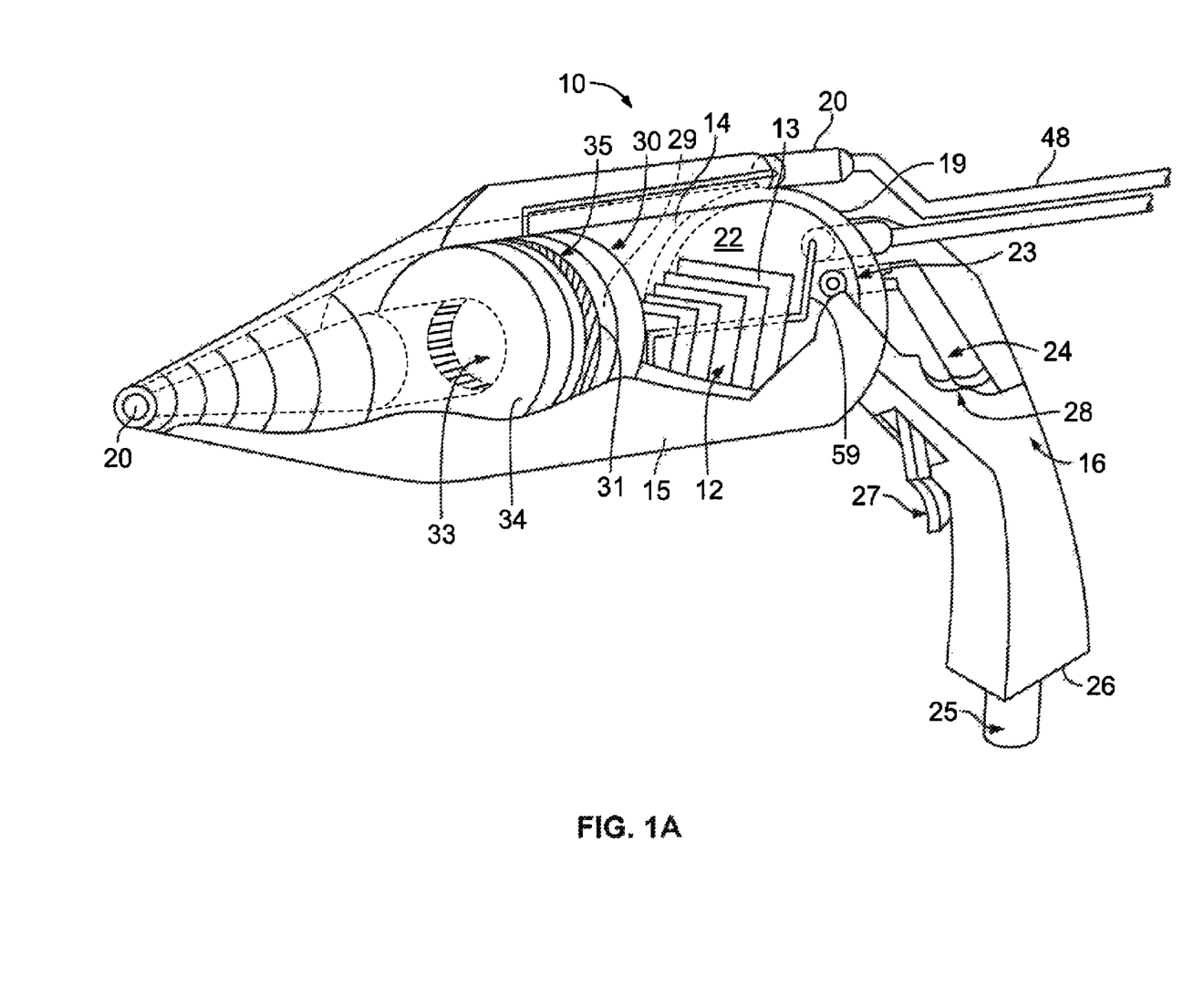
FIGS. 1A and 1B are cutaway views of the hand-held atmospheric harmonic cold plasma device, in accordance with embodiments of the present invention.

To achieve a cold plasma, a cold plasma device typically takes as input a source of appropriate gas and a source of high voltage electrical energy, and outputs a plasma plume. FIG. 1A illustrates such a cold plasma device. Previous work by the inventors in this research area has been described in U.S. Provisional Patent Application No. 60/913,369, U.S. Non-provisional application Ser. No. 12/038,159 (that has issued as U.S. Pat. No. 7,633,231) and the subsequent continuation applications (collectively "the '369 application family"). The following paragraphs discuss further the subject matter from this application family further, as well as additional developments in this field.

The '369 application family describes a cold plasma device that is supplied with helium gas, connected to a high voltage energy source, and which results in the output of a cold plasma. The temperature of the cold plasma is approximately 65-120 degrees F. (preferably 65-99 degrees F.), and details of the electrode, induction grid and magnet structures are described. The voltage waveforms in the device are illustrated at a typical operating point in '369 application family.

Figure 1B:
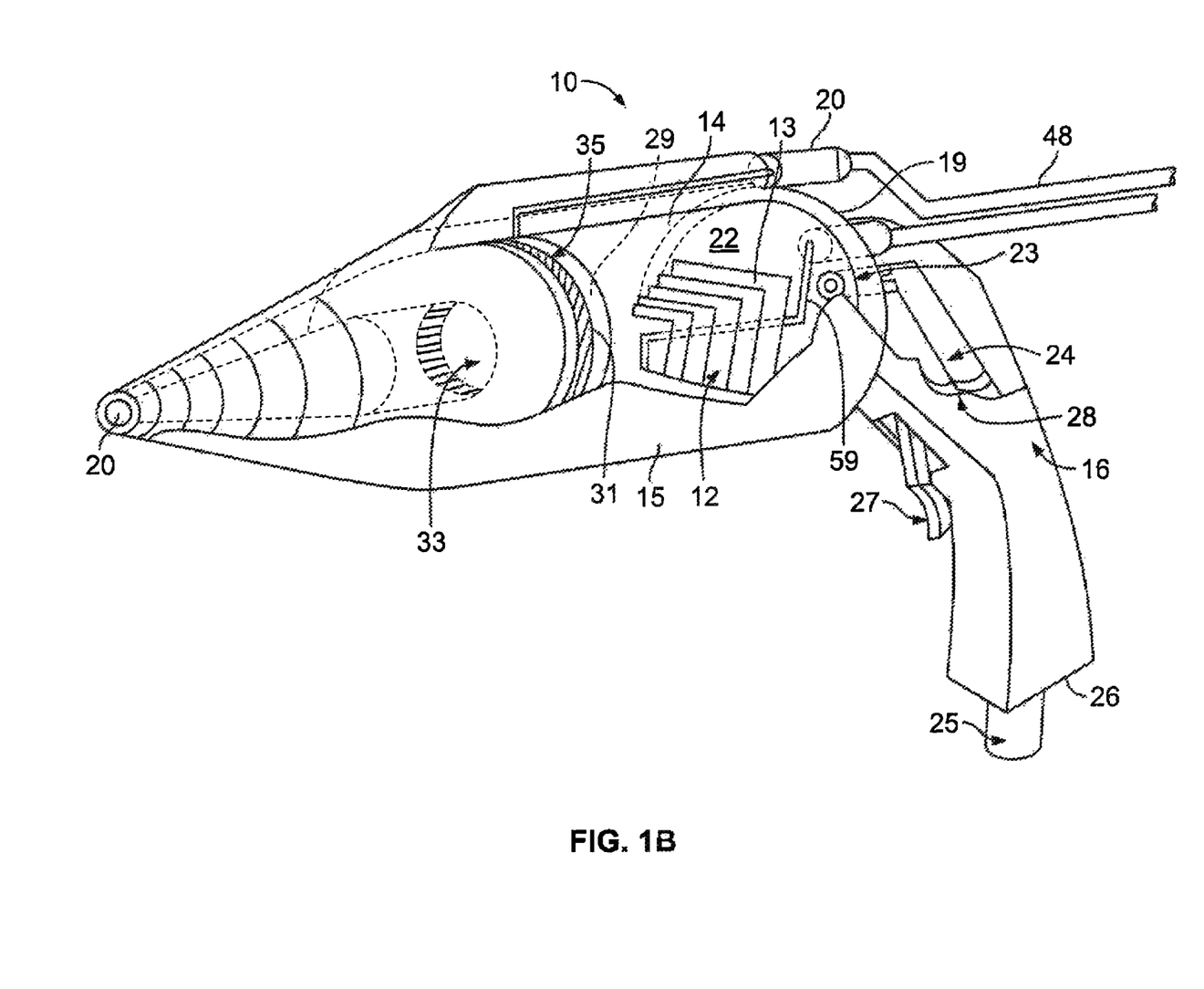
Figure 2A:
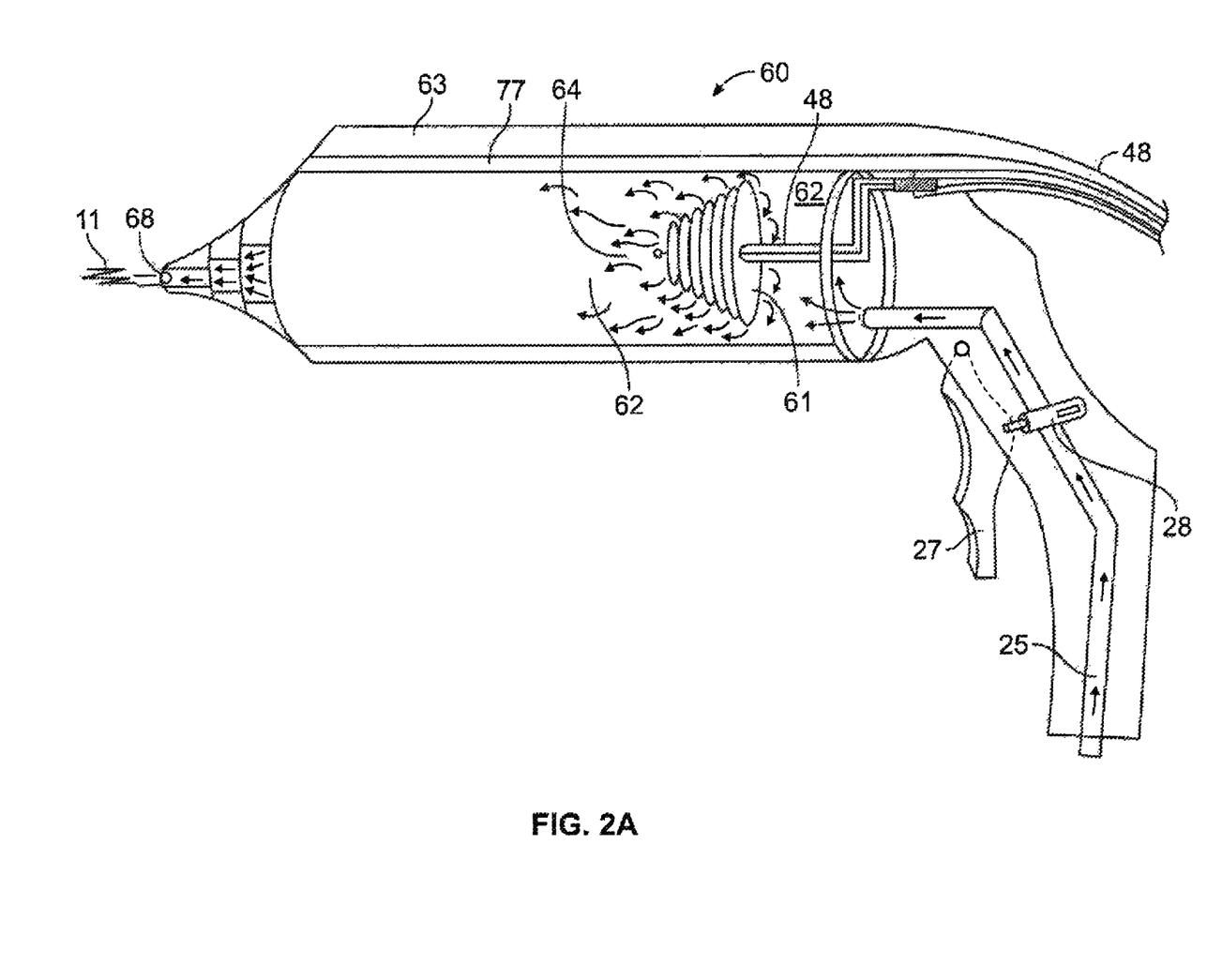
FIGS. 2A and 2B illustrate an embodiment of the cold plasma device without magnets, in accordance with embodiments of the present invention.
Figure 2B:
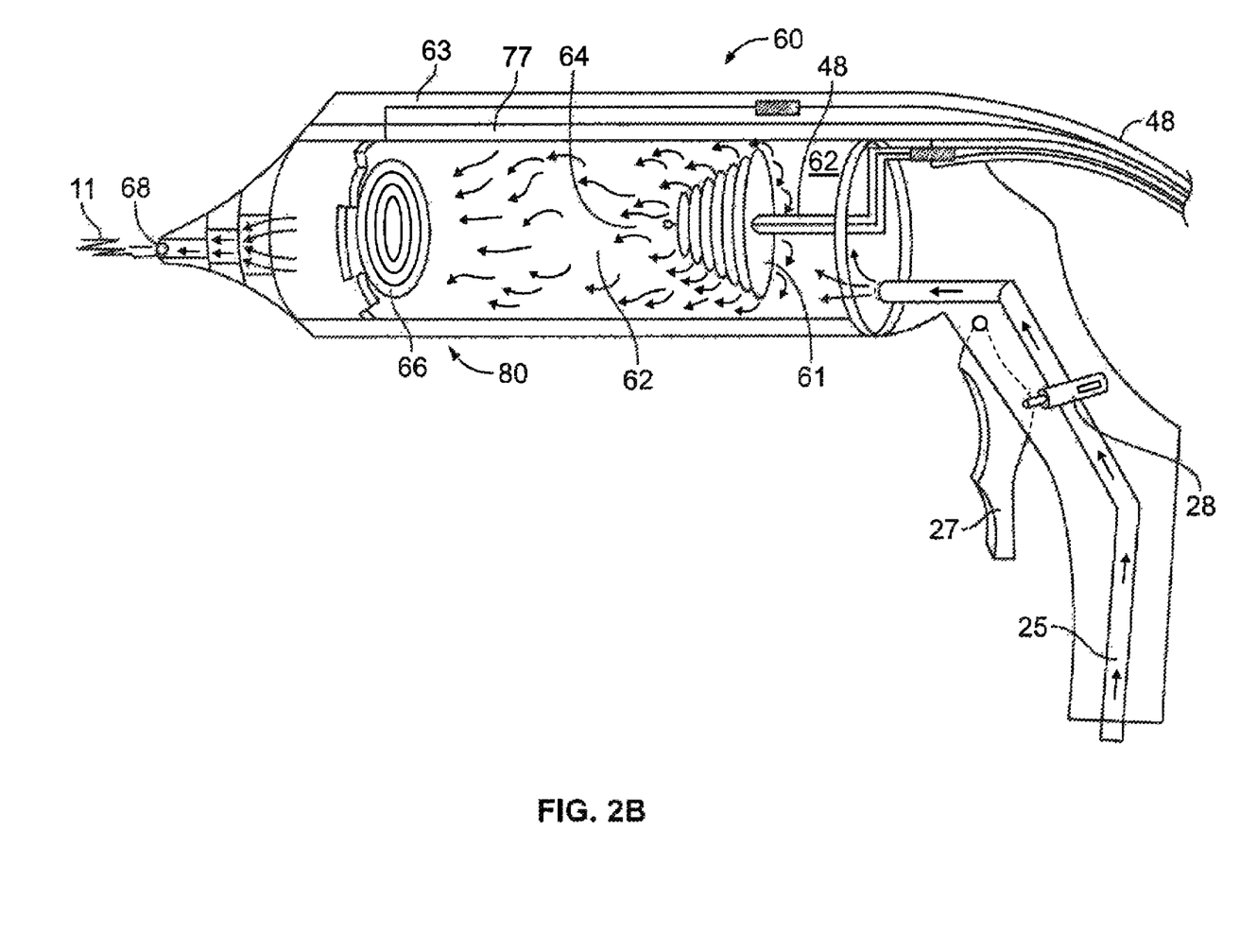

In a further embodiment to that described in the '369 application, plasma is generated using an apparatus without magnets, as illustrated in FIGS. 2A and 2B. In this magnet-free environment, the plasma generated by the action of the electrodes 61 is carried with the fluid flow downstream towards the nozzle 68. FIG. 2A illustrates a magnet-free embodiment in which no induction grid is used. FIG. 2B illustrates a magnet-free embodiment in which induction grid 66 is used. FIG. 1B illustrates the same embodiment as illustrated in FIG. 2B, but from a different view. Although these embodiments illustrate the cold plasma is generated from electrode 12, other embodiments do not power the cold plasma device using electrode 12, but instead power the cold plasma device using induction grid 66.

In both a magnet and a magnet-free embodiment, the inductance grid 66 is optional. When inductance grid 66 is present, it provides ionization energy to the gas as the gas passes by. Thus, although the inductance grid 66 is optional, its presence enriches the resulting plasma.

As noted above, the inductance grid 66 is optional. When absent, the plasma will nevertheless transit the cold plasma device and exit at the nozzle 68, although in this case, there will be no additional ionization energy supplied to the gas as it transits the latter stage of the cold plasma device.

As noted with respect to other embodiments, magnetic fields can be used in conjunction with the production of cold plasmas. Where present, magnetic fields act, at least at some level, to constrain the plasma and to guide it through the device. In general, electrically charged particles tend to move along magnetic field lines in spiral trajectories. As noted elsewhere, other embodiments can comprise magnets configured and arranged to produce various magnetic field configurations to suit various design considerations. For example, in one embodiment as described in the previously filed '369 application family, a pair of magnets may be configured to give rise to magnetic fields with opposing directions that act to confine the plasma near the inductance grid.

Cold Plasma Unipolar High Voltage Power Supply

The '369 application family also illustrates an embodiment of the unipolar high voltage power supply architecture and components used therein. The circuit architecture is reproduced here as FIG. 3, and this universal power unit provides electrical power for a variety of embodiments described further below. The architecture of this universal power unit includes a low voltage timer, followed by a preamplifier that feeds a lower step-up voltage transformer. The lower step-up voltage transformer in turn feeds a high frequency resonant inductor-capacitor (LC) circuit that is input to an upper step-up voltage transformer. The output of the upper step-up voltage transformer provides the output from the unipolar high voltage power supply.

Figure 3:
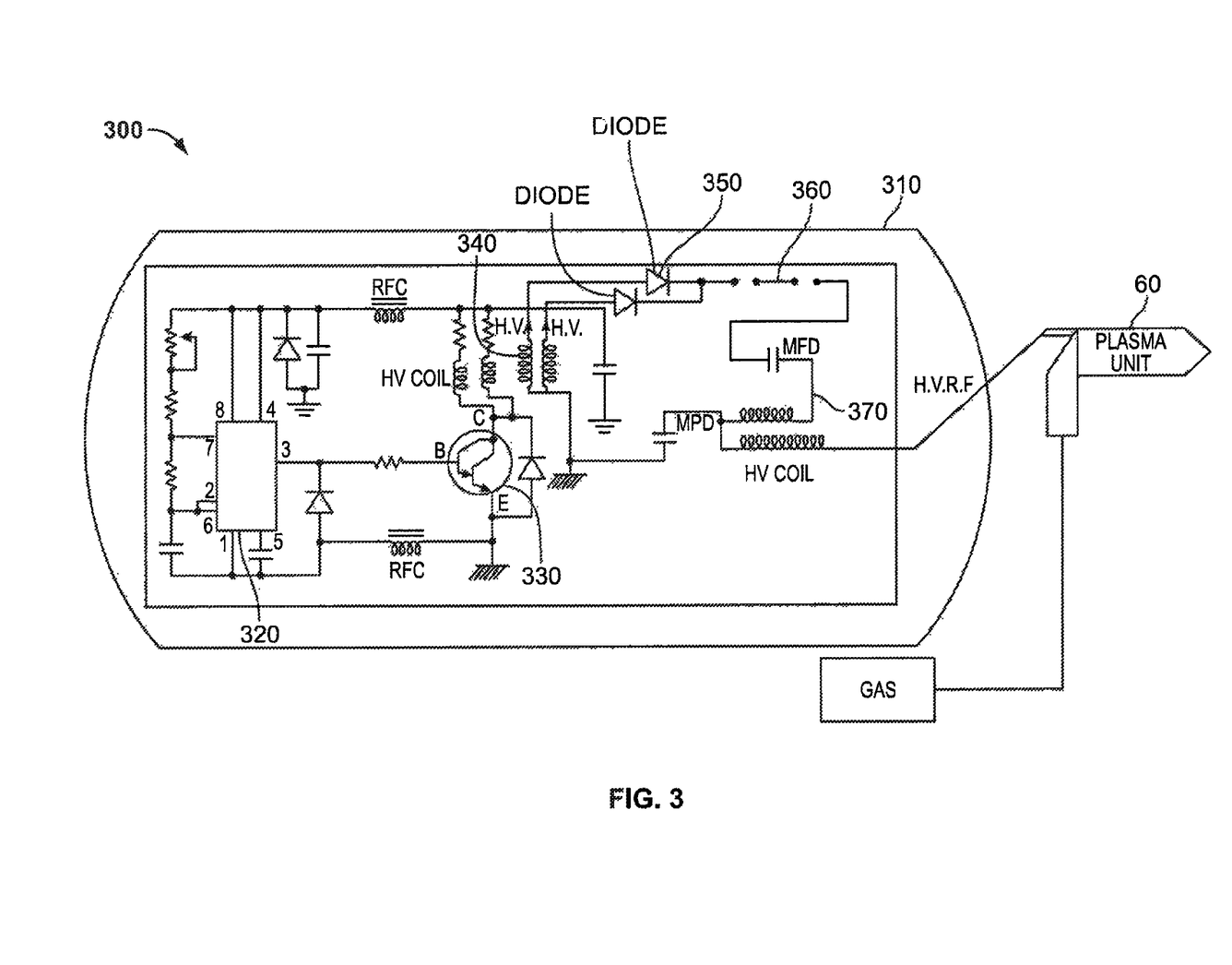
FIG. 3 is an exemplary circuit diagram of the power supply of a cold plasma device, in accordance with embodiments of the present invention.

FIG. 3 also illustrates an exemplary implementation of the unipolar high voltage power supply 310 architecture. In this implementation, a timer integrated circuit such as a 555 timer 320 provides a low voltage pulsed source with a frequency that is tunable over a frequency range centered at approximately 1 kHz. The output of the 555 timer 320 is fed into a preamplifier that is formed from a common emitter bipolar transistor 330 whose load is the primary winding of the lower step-up voltage transformer 340. The collector voltage of the transistor forms the output voltage that is input into the lower step-up voltage transformer. The lower step-up transformer provides a magnification of the voltage to the secondary windings. In turn, the output voltage of the lower step-up voltage transformer is forwarded to a series combination of a high voltage rectifier diode 350, a quenching gap 360 and finally to a series LC resonant circuit 370. As the voltage waveform rises, the rectifier diode conducts, but the quench gap voltage will not have exceeded its breakdown voltage. Accordingly, the quench gap is an open circuit, and therefore the capacitor in the series LC resonant circuit will charge up. Eventually, as the input voltage waveform increases, the voltage across the quench gap exceeds its breakdown voltage, and it arcs over and becomes a short circuit. At this time, the capacitor stops charging and begins to discharge. The energy stored in the capacitor is discharged via the tank circuit formed by the series LC connection.

Continuing to refer to FIG. 3, the inductor also forms the primary winding of the upper step-up voltage transformer 340. Thus, the voltage across the inductor of the LC circuit will resonate at the resonant frequency of the LC circuit 370, and in turn will be further stepped-up at the secondary winding of the upper step-up voltage transformer. The resonant frequency of the LC circuit 370 can be set to in the high kHz-low MHz range. The voltage at the secondary winding of the upper step-up transformer is connected to the output of the power supply unit for delivery to the cold plasma device. The typical output voltage is in the 10-150 kV voltage range. Thus, voltage pulses having a frequency in the high kHz-low MHz range can be generated with an adjustable repetition frequency in the 1 kHz range. The output waveform is shaped similar to the acoustic waveform generated by an impulse such as when a bell is struck with a hammer. Here, the impulse is provided when the spark gap or a silicon controlled rectifier (SCR) fires and produces the voltage pulse which causes the resonant circuits in the primary and secondary sides of the transformer to resonate at their specific resonant frequencies. The resonant frequencies of the primary and the secondary windings are different. As a result, the two signals mix and produce the unique 'harmonic' waveform seen in the transformer output. The net result of the unipolar high voltage power supply is the production of a high voltage waveform with a novel "electrical signature," which when combined with a noble gas or other suitable gas, produces a unique harmonic cold plasma that provides advantageous results in wound healing, bacterial removal and other applications.

The quenching gap 360 is a component of the unipolar high voltage power supply 310. It modulates the push/pull of electrical energy between the capacitance banks, with the resulting generation of electrical energy that is rich in harmonic content. The quenching gap can be accomplished in a number of different ways, including a sealed spark gap and an unsealed spark gap. The sealed spark gap is not adjustable, while unsealed spark gaps can be adjustable, for example by varying the distance between the spark gap electrodes. A sealed spark gap can be realized using, for example, a DECI-ARC 3000 V gas tube from Reynolds Industries, Inc. Adjustable spark gaps provide the opportunity to adjust the output of the unipolar high voltage power supply and the intensity of the cold plasma device to which it is connected. In a further embodiment of the present invention that incorporates a sealed (and therefore non-adjustable) spark gap, thereby ensuring a stable plasma intensity.

In an exemplary embodiment of the unipolar high voltage power supply, a 555 timer 320 is used to provide a pulse repetition frequency of approximately 150-600 Hz. As discussed above, the unipolar high voltage power supply produces a series of spark gap discharge pulses based on the pulse repetition frequency. The spark gap discharge pulses have a very narrow pulse width due to the extremely rapid discharge of capacitive stored energy across the spark gap. Initial assessments of the pulse width of the spark gap discharge pulses indicate that the pulse width is approximately 1 nsec. The spark gap discharge pulse train can be described or modeled as a filtered pulse train. In particular, a simple resistor-inductor-capacitor (RLC) filter can be used to model the capacitor, high voltage coil and series resistance of the unipolar high voltage power supply. In one embodiment of the invention, the spark gap discharge pulse train can be modeled as a simple modeled RLC frequency response centered in the range of around 100 MHz. Based on the pulse repetition frequency of 192 Hz, straightforward signal analysis indicates that there would be approximately 2,000,000 individual harmonic components between DC and 400 MHz.

In another embodiment of the unipolar high voltage power supply described above, a 556 timer or any timer circuit can be used in place of the 555 timer 320. In comparison with the 555 timer, the 556 timer provides a wider frequency tuning range that results in greater stability and improved cadence of the unipolar high voltage power supply when used in conjunction with the cold plasma device.

Cold Plasma Dielectric Barrier Discharge Device

Figure 4:
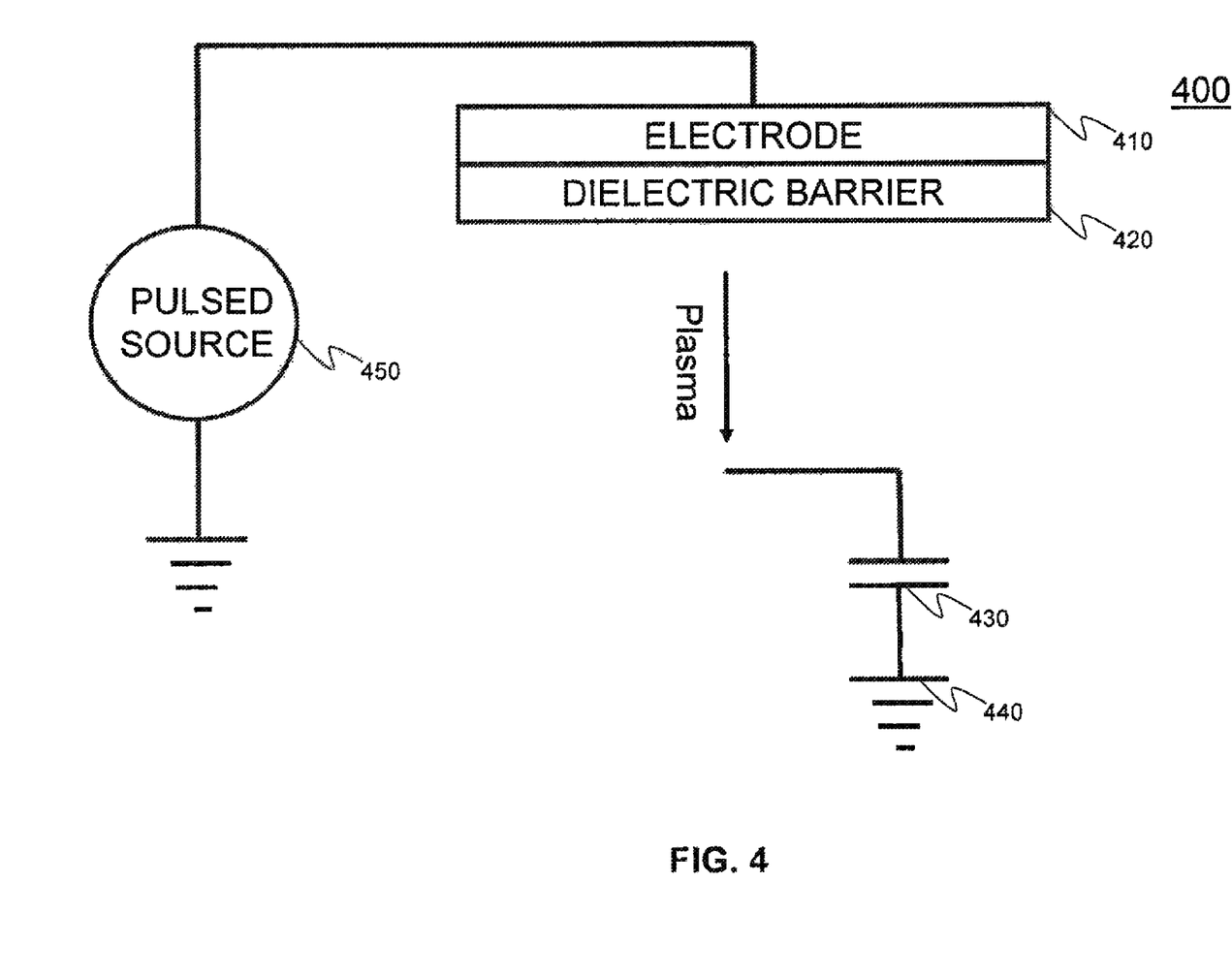
FIG. 4 illustrates the generation of cold plasma resulting from a dielectric barrier discharge device, in accordance with embodiments of the present invention, in accordance with embodiments of the present invention.

Devices, other than the cold plasma device illustrated above in FIGS. 1A, 1B, 2A and 2B, can also generate cold plasma. For example, cold plasma can also be generated by a dielectric barrier device, which relies on a different process to generate the cold plasma. DBD plasmas are generally created in a non-equilibrium mode by passing electrical discharges over a small distance through ambient air. As FIG. 4 illustrates, a dielectric barrier device (DBD) 400 contains one metal electrode 410 covered by a dielectric layer 420. The electrical return path 430 is formed by the ground 440 that can be provided by the target substrate or the subject undergoing the cold plasma treatment. Energy for the dielectric barrier device 400 can be provided by a power supply 450, such as that described above and illustrated in FIG. 3. More generally, energy is input to the dielectric barrier device in the form of pulsed electrical voltage to form the plasma discharge. By virtue of the dielectric layer, the discharge is separated from the metal electrode and electrode etching is reduced. The pulsed electrical voltage can be varied in amplitude and frequency to achieve varying regimes of operation. The gas used can be ambient air, a biocompatible gas, or the like. In other embodiments, gases other than ambient air can be supplied at the inbound side of a plasma generating module to achieve an optimal or desired plasma chemistry for treatment or other useful purposes.

Additional Cold Plasma Unipolar Power Supply Embodiment

Figure 5:
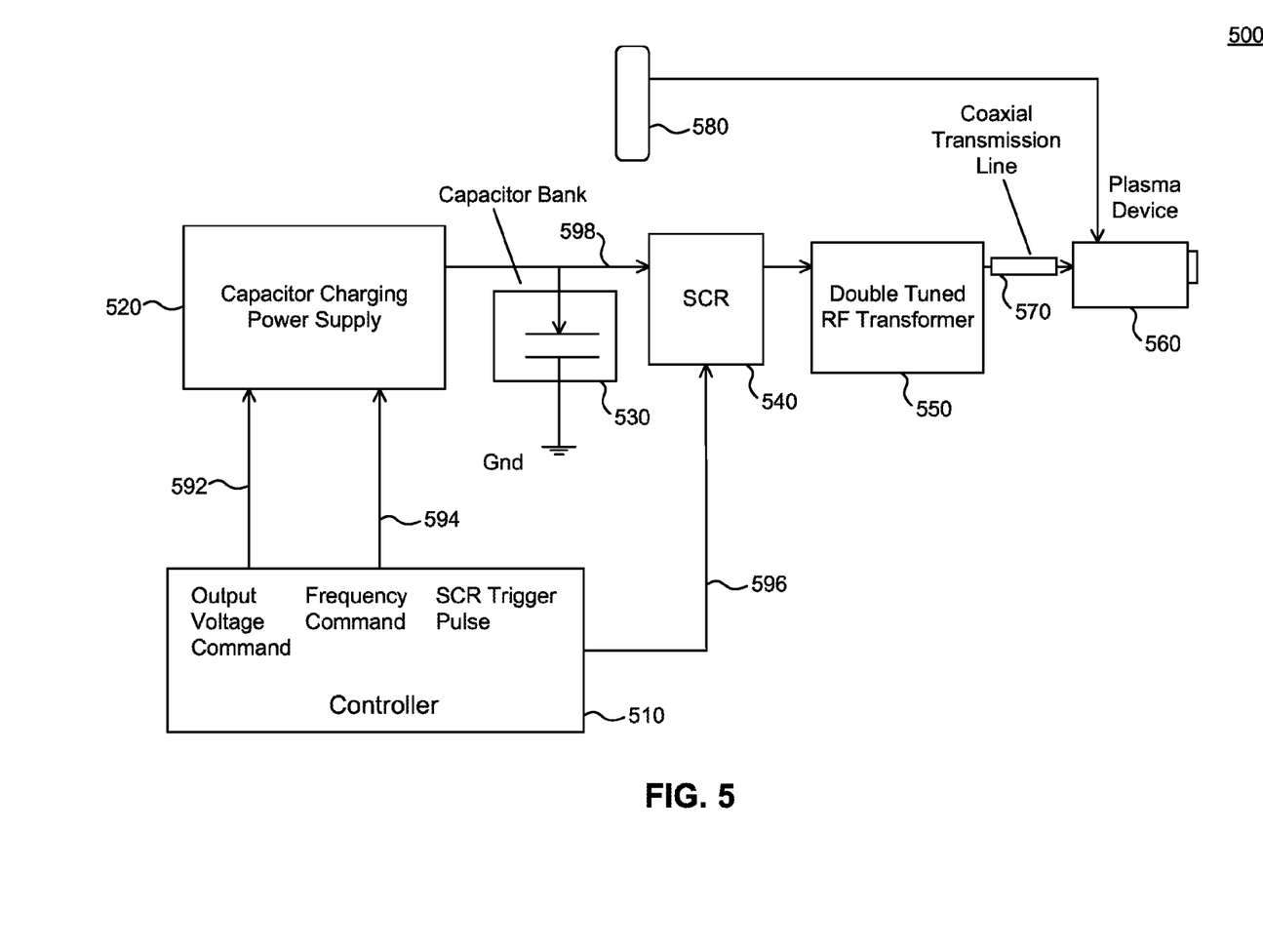
FIG. 5 illustrates an exemplary cold plasma high voltage power supply, in accordance with an embodiment of the present invention.

As noted above, both the cold plasma devices of the type illustrated in FIGS. 1A, 1B, 2A and 2B, as well as the DBD-type device illustrated in FIG. 4, required electrical energy from a suitable power supply. An alternate embodiment of a suitable power supply is illustrated in FIG. 5. A capacitor charging power supply 520 provides a current source that charges capacitor bank 530 to a desired voltage. The desired voltage can be set by an output voltage command 592 from a controller 510. Controller 510 also issues a frequency command 594 to capacitor charging power supply 520 such that charging occurs on the positive half of the frequency command cycle. Capacitor bank 530 includes one or more capacitors that receive and store the electrical energy from the current source in capacitor charging power supply 520. A controllable switch (e.g., silicon controlled rectifier (SCR)) 540 is coupled to capacitor bank 530 and capacitor charging power supply 520. Controllable switch 540 closes and forwards the energy from capacitor bank 530 to double tuned RF transformer 550. Controllable switch 540 closes upon receipt of a trigger pulse 596 from controller 510. Trigger pulse 596 occurs on the negative half of the frequency command cycle, i.e., the opposite half cycle to the charging portion of the frequency command cycle.

Double tuned RF transformer 550 has a primary winding and a secondary winding. The voltage from controllable switch 540 passes to the primary winding, with a resulting voltage appearing on the secondary winding. Double tuned RF transformer 550 is configured to resonate at two different frequencies, one resonant frequency is associated with the primary winding and the second resonant frequency is associated with the secondary winding. The primary winding resonance is an inductor-capacitor (LC) resonance that results from the series combination of the primary winding inductance with the capacitance of the capacitance bank 530. The secondary winding resonance is an inductor-capacitor (LC) resonance that results from the series combination of the secondary winding inductance with the capacitance of coaxial transmission line 570 together with any capacitance resulting from plasma device 560. The two resonant frequencies are different, which leads to a harmonic rich waveform that is applied to plasma device 560. In an exemplary embodiment, the resonant frequencies are 320 kHz and 470 kHz. As noted above, plasma device 560 can be any cold plasma device of the type illustrated in FIGS. 1A, 1B, 2A, 2B and 4.

Output voltage command 592 and frequency command 594 provide the ability to adjust the energy stored in capacitor bank 530, the energy that is therefore input to double tuned RF transformer 550, and therefore the energy that is input to plasma device 560. Therefore, depending on the choice of gas from gas container 580 (e.g., gas cartridge) and the type of plasma device 560 (e.g., cold plasma gun, cold plasma DBD device), as well as the type of treatment protocol, the energy can be adjusted to provide the appropriate setting for those choices.

Further to this flexibility, in a further embodiment, various components of the cold plasma device illustrated in FIGS. 1A, 1B, 2A and 2B can be provided in a modular fashion, such that these components can be inserted into the cold plasma device individually. Thus, modular versions of the electrode, magnets and induction grid can be provided such that the user can individually select the presence (or absence) of each of these components depending on the choice of gas and treatment protocol. Thus, for example, a particular treatment protocol may require the presence of only the electrode, in which case the magnet and induction grid can be removed by the user. Similarly, another particular treatment protocol may require the presence of the electrode, magnet and induction grid and therefore the user would add these three components to the cold plasma device prior to beginning the treatment.

Cold Plasma Methods

Figure 6:
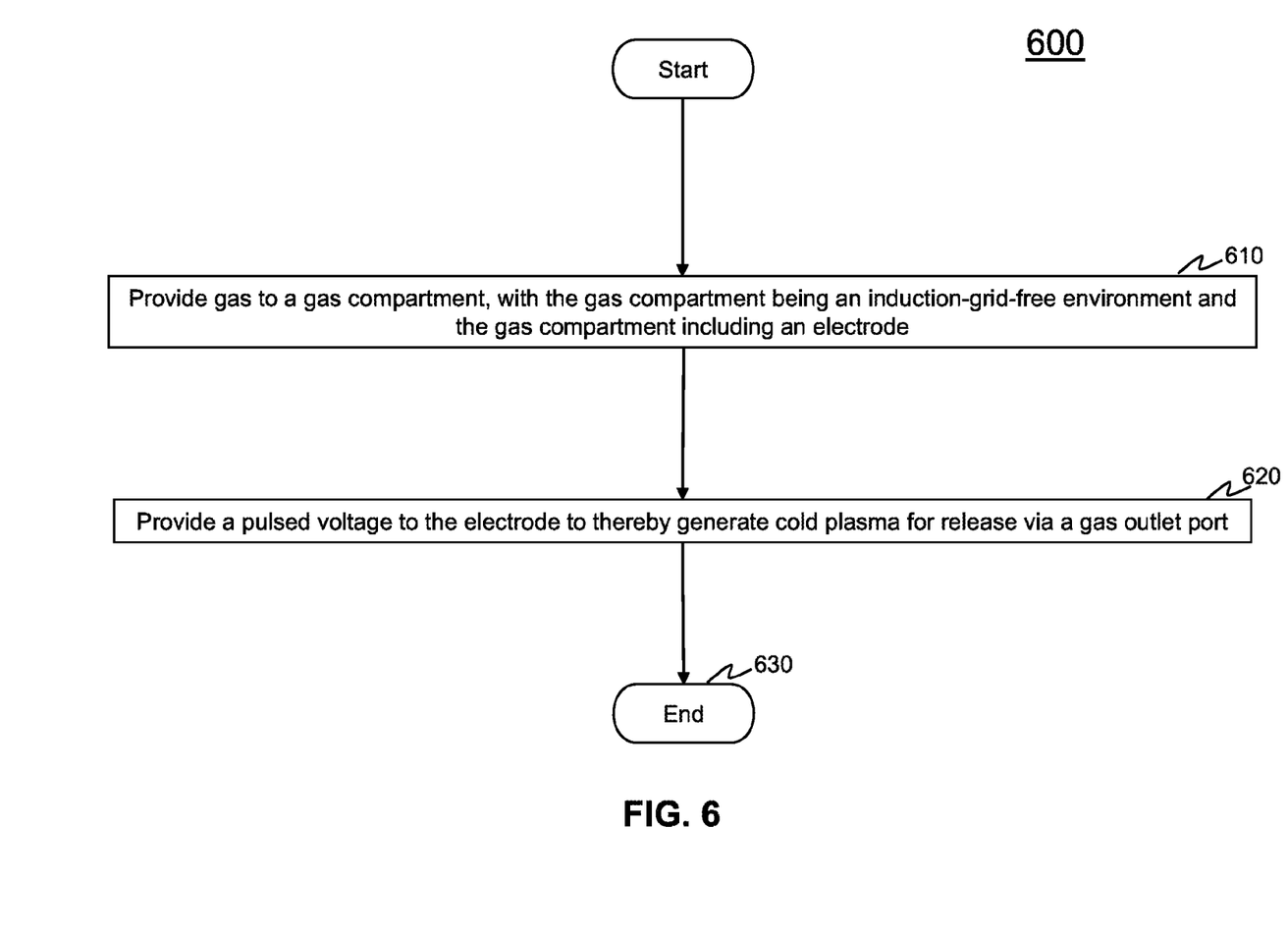
FIG. 6 illustrates an exemplary method of use of an induction-grid-free cold plasma device, in accordance with an embodiment of the present invention.

FIG. 6 provides a flowchart of an exemplary method 600 of use of an induction-grid-free cold plasma device, according to an embodiment of the present invention.

The process begins at step 610. In step 610, gas is provided to a gas compartment via a gas inlet port, with the gas compartment being an induction-grid-free environment located within a housing having a high voltage electrical inlet port coupled to an electrode disposed within the gas compartment.

In step 620, a pulsed voltage is provided to the electrode via the high voltage electrical inlet port to thereby generate cold plasma for release via a gas outlet port of the gas compartment, the cold plasma having a temperature in a range of 65 to 120 degrees Fahrenheit.

At step 630, method 600 ends.

Figure 7:
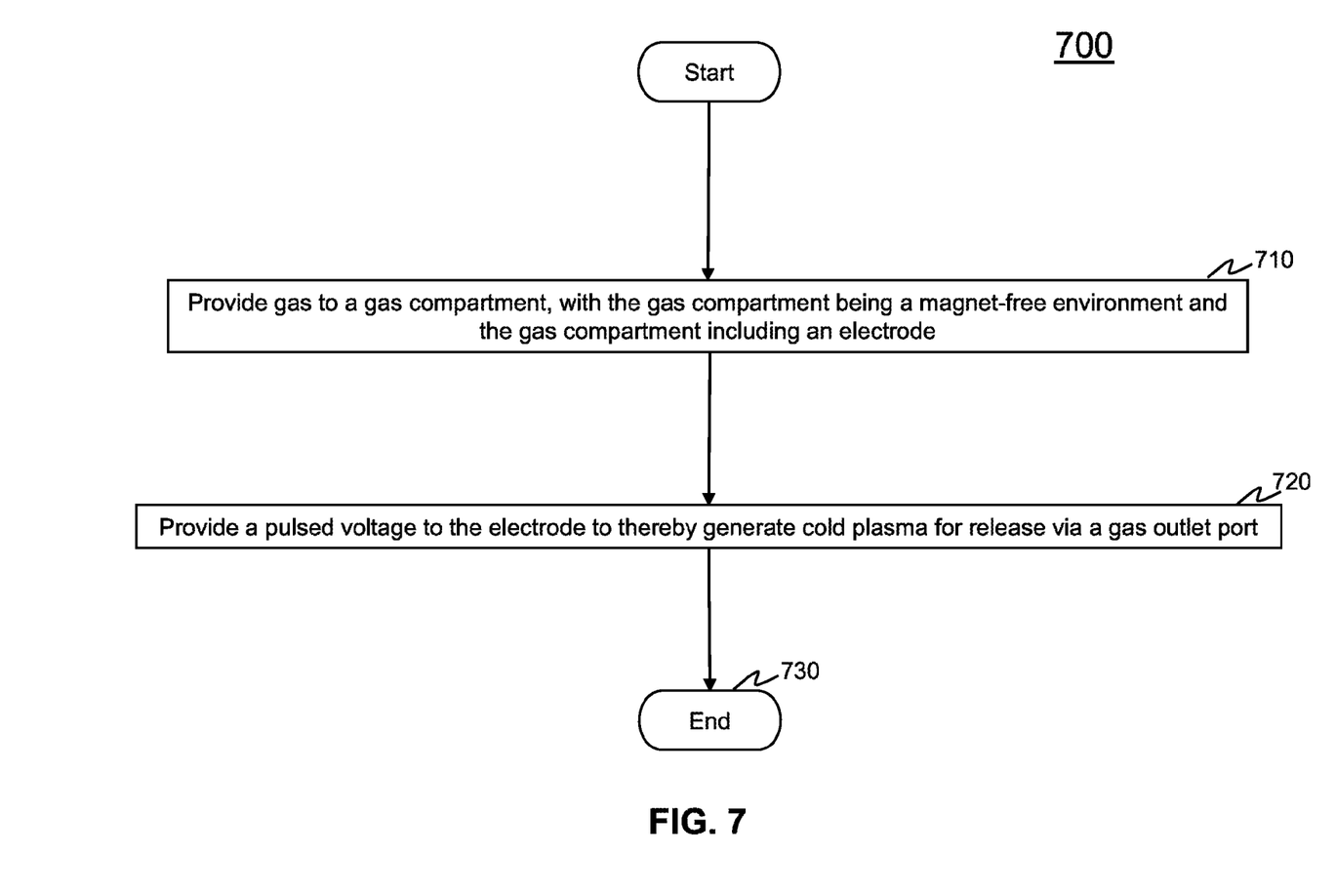
FIG. 7 illustrates an exemplary method of use of a magnet-free cold plasma device, in accordance with an embodiment of the present invention.

FIG. 7 provides a flowchart of an exemplary method 700 of use of a magnet-free cold plasma device, according to an embodiment of the present invention.

The process begins at step 710. In step 710, gas is provided to a gas compartment via a gas inlet port, with the gas compartment being a magnet-free environment located within a housing having a high voltage electrical inlet port coupled to an electrode disposed within the gas compartment.

In step 720, a pulsed voltage is provided to the electrode via the high voltage electrical inlet port to thereby generate cold plasma for release via a gas outlet port of the gas compartment, the cold plasma having a temperature in a range of 65 to 120 degrees Fahrenheit.

At step 730, method 700 ends.

Figure 8:
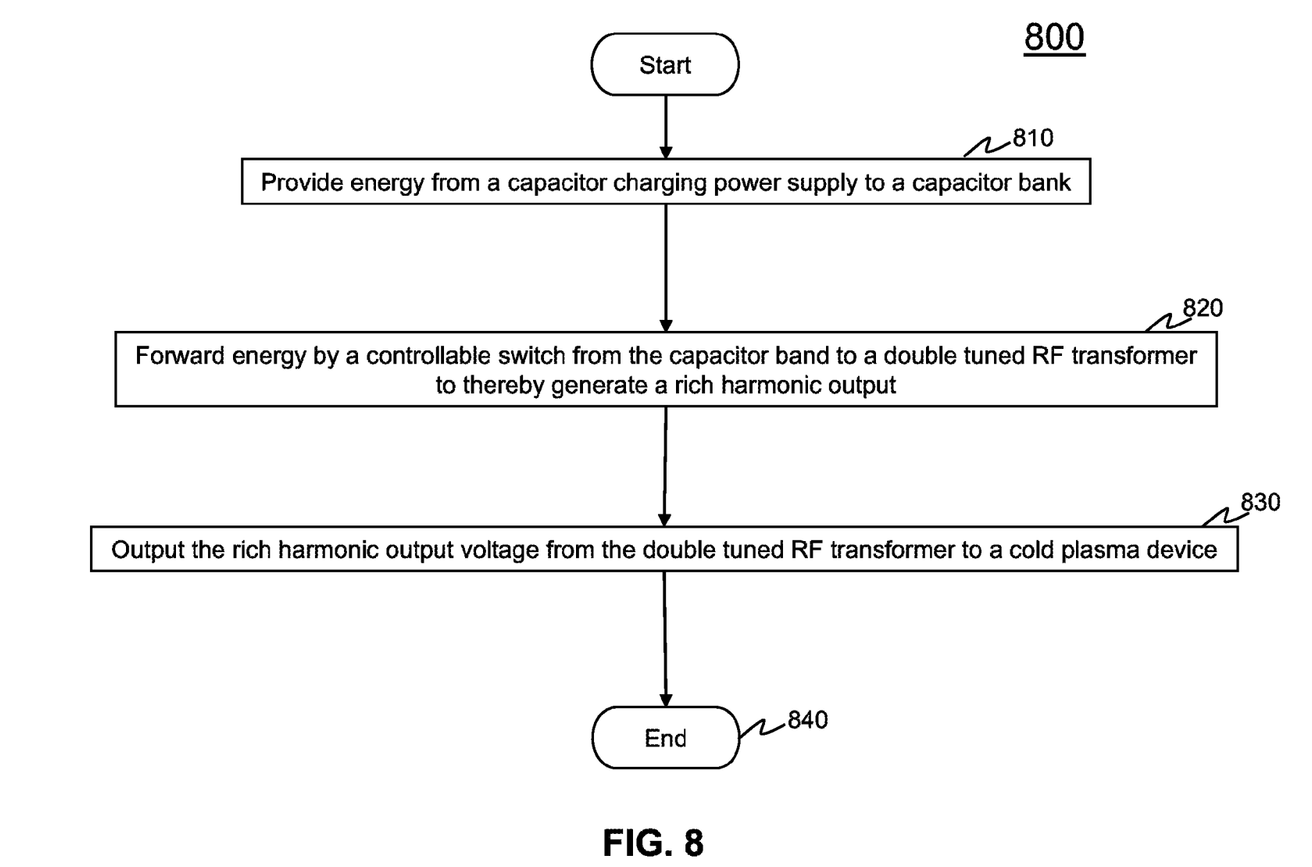
FIG. 8 illustrates an exemplary method to provide a high voltage power signal for use with a cold plasma device, in accordance with an embodiment of the present invention.

FIG. 8 provides a flowchart of an exemplary method 800 to provide a high voltage power signal for use with a cold plasma device, according to an embodiment of the present invention.

The process begins at step 810. In step 810, energy is provided from a capacitor charging power supply to a capacitor bank having one or more capacitors. In an embodiment, energy is provided from a capacitor charging power supply 520 to a capacitor bank 530 having one or more capacitors.

In step 820, the energy is forwarded by a controllable switch from the capacitor bank to a double tuned RF transformer to thereby generate a rich harmonic output voltage. In an embodiment, the energy is forwarded by a controllable switch 540 from the capacitor bank 530 to a double tuned RF transformer 550 to thereby generate a rich harmonic output voltage.

In step 830, the rich harmonic output voltage is output from the double tuned RF transformer to a cold plasma device. In an exemplary embodiment, the rich harmonic output voltage is output from the double tuned RF transformer 550 to a cold plasma device 560.

At step 840, method 800 ends.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A cold plasma device, comprising:
    a cold plasma high voltage power supply including:
        a capacitor charging power supply having one or more command inputs;
        a capacitor bank having one or more capacitors, the capacitor bank being coupled to the capacitor charging power supply;
        a controllable switch coupled to the capacitor bank;
        a double tuned RF transformer having, an input and an output, the input coupled to the controllable switch, the double tuned RF transformer configured to resonate at a first frequency and at a second frequency, wherein the resonance at the second frequency results, in part, from a capacitance of a transmission line coupled to the output;
        a controller configured to provide commands to the one or more command inputs of the capacitor charging power supply, and to provide a trigger pulse to the controllable switch;
    a housing having a high voltage electrical inlet port configured to receive a harmonic rich power signal from the output of the double tuned RF transformer via the transmission line;
    a gas compartment disposed within the housing, wherein the gas compartment is an induction-grid-free environment, and wherein the gas compartment includes a gas inlet port to receive a gas flow of gas and a gas outlet port; and
    an electrode disposed within the gas compartment, wherein the electrode is coupled to the high voltage electrical inlet port, wherein the electrode comprises one or more components configured to resonate at frequencies associated with the harmonic rich power signal, and wherein the electrode is configured to generate cold plasma for release via the gas outlet port, the cold plasma having a temperature in a range of 65 to 120 degrees Fahrenheit.

2. The cold plasma device of claim 1, wherein the gas compartment further includes an induction grid coupled to the high voltage electrical inlet port to thereby interact with the gas.

3. The cold plasma device of claim 1, wherein the gas compartment further includes an induction grid coupled to the high voltage electrical inlet port, the induction grid being configured to provide ionization energy to the gas.

4. The cold plasma device of claim 3, wherein the induction grid is modular, and is associated with the gas and a treatment protocol, the modular induction grid being configured for easy insertion and removal from the gas compartment.

5. The cold plasma device of claim 1, wherein the gas comprises a noble gas.

6. The cold plasma device of claim 1, wherein the gas comprises helium.

7. The cold plasma device of claim 1, wherein the gas compartment further includes a magnet configured to at least partially direct the cold plasma.

8. The cold plasma device of claim 1, wherein the controllable switch comprises a silicon controlled rectifier (SCR).

9. The cold plasma device of claim 1, wherein the commands include one or more of an output voltage command and a frequency command.

10. The cold plasma device of claim 1, wherein the resonance at the first frequency results, in part, from capacitance of the capacitor bank and an inductance of a primary winding of the double tuned RF transformer.

11. A method, comprising:
    receiving, at a capacitor bank having one or more capacitors, energy from a capacitor charging power supply;
    switching, using a controllable switch, a coupling between the capacitor bank and a double tuned RF transformer;
    resonating, by the double tuned RF transformer, at a first frequency and at a second frequency to thereby provide a harmonic rich power signal, wherein the resonating at the second frequency results, in part, from a capacitance of a transmission line coupled to an output of the double tuned RF transformer;
    providing gas to a gas compartment via a gas inlet port, the gas compartment being an induction-grid-free environment located within a housing having a high voltage electrical inlet port coupled to an electrode disposed within the gas compartment; and
    providing the harmonic rich power signal to the electrode via the high voltage electrical inlet port to thereby generate cold plasma for release via a gas outlet port of the gas compartment, the cold plasma having a temperature in a range of 65 to 120 degrees Fahrenheit, wherein the electrode comprises one or more components configured to resonate at frequencies associated with the harmonic rich power signal received via the high voltage electrical inlet port.

12. The method of claim 11, further comprising:
    providing, using a magnet, a magnetic field within the gas compartment to at least partially direct the cold plasma.

13. The method of claim 11, further comprising:
    providing the harmonic rich power signal to an induction grid via the high voltage electrical inlet port to thereby interact with the gas.

14. The method of claim 11, wherein the gas comprises a noble gas.

15. The method of claim 11, wherein the gas comprises helium.

16. The method of claim 11, further comprising:
    adjusting, using a controller, the switching using a trigger command to the controllable switch.

17. The method of claim 11, further comprising:
    adjusting, using a controller, the energy using an output voltage command to the capacitor charging power supply.

18. The method of claim 11, further comprising:
    adjusting, using a controller, the energy using a frequency command to the capacitor charging power supply.

19. The method of claim 11, wherein the switching using the controllable switch includes switching using a silicon controlled rectifier (SCR).

20. The method of claim 11, wherein the resonating at the first frequency results, in part, from capacitance of the capacitor bank and an inductance of a primary winding of the double tuned RF transformer.

* * * * *